US006906100B2

(12) United States Patent
Fotinos et al.

(10) Patent No.: US 6,906,100 B2
(45) Date of Patent: Jun. 14, 2005

(54) COMPOUNDS AND COMPOSITIONS DERIVED FROM OLIVES AND METHODS OF THE USE THEREOF

(75) Inventors: Spiros Fotinos, Athens (GR); Ligia Panaitescu, Attiki (GR); Alexios-Leandros Skaltsounis, Athens (GR); Sofia Mitakou, Athens (GR); Prokopios Magiatis, Salamina (GR); Nektarios Aligiannis, Nea Peramos Megaridos (GR); Dimitrios Galaris, Ioannina (GR)

(73) Assignee: Lavipharm S.A. (GR)

(*) Notice: Subject to any disclaimer, the term of this patent is extended or adjusted under 35 U.S.C. 154(b) by 0 days.

(21) Appl. No.: 10/364,305

(22) Filed: Feb. 10, 2003

(65) Prior Publication Data

US 2003/0185921 A1 Oct. 2, 2003

(30) Foreign Application Priority Data

Feb. 8, 2002 (GR) ........................................ 20020100071
Feb. 8, 2002 (GR) ........................................ 20020100072

(51) Int. Cl.$^7$ ............................................. A61K 31/35
(52) U.S. Cl. ...................................................... 514/460
(58) Field of Search ........................ 514/460; 549/291; 424/725

(56) References Cited

U.S. PATENT DOCUMENTS

| 6,361,803 | B1 | * | 3/2002 | Cuomo et al. | ............... | 424/725 |
| 6,416,808 | B1 | * | 7/2002 | Crea | ........................... | 426/601 |
| 6,455,580 | B1 | * | 9/2002 | Fredrickson | ................ | 514/460 |
| 2002/0004077 | A1 | * | 1/2002 | Cuomo et al. | ............... | 424/725 |

FOREIGN PATENT DOCUMENTS

| EP | 0811678 | 12/1997 |
| ES | 2145701 | 7/2000 |
| JP | 8119825 | 5/1996 |
| RU | 2151137 | 6/2000 |
| WO | WO 02/16628 | 2/2002 |
| WO | WO 02/18310 | 3/2002 |

OTHER PUBLICATIONS

Martindale, The Extra Pharmacopoeia, 28$^{th}$ edition, Published 1982 by The Pharmaceutical Press, (London) p. 697.*
Barbouti, et al., 2000, "DNA Damage and Apoptosis in Hydrogen Peroxide–Exposed Jurkat Cells: Bolus Addition versus Continuous Generation of $H_2O_2$, " *Free Radical Biology & Medicine*, 2002, pp. 691–702, vol. 33, No. 5.
De La Cruz, et al., May 2000, "Lipid Peroxidation and Glutathione System in Hyperlipemic Rabbits: Influenece of Olive Oil Administration," *Molecular and Cell Biology of Lipids*, May 2000, pp. 36–44, vol. 1485, No. 1.
Johnson, et al., Apr. 28, 2000, "Effects of Epigallocatechin Gallate and Quercetin on Oxidative Damage to Cellular DNA," *Mutation Research*, pp. 211–218, vol. 459, No. 3, Apr. 28, 2000.
Manna, et al., Mar. 2000, "Transport Mechanism and Metabolism of Olive Oil Hydroxytyrosol in Caco-2 Cells," *FEBS Letters*, Mar. 2000, pp. 341–344, vol. 470, No. 3.
Deiana, et al., Mar. 1999, "Inhibition of Peroxynitrite Dependent DNA Base Modification and Tyrosine Nitration by the Extra Vigin Olive Oil–Derived Antioxidant Hydroxytyrosol," *Free Radical Biology & Medicine*, Mar. 1999, pp. 762–769, vol. 26, Nos. 5/6.
Gil, et al., Nov. 1998, "Two Glutaric Acid Derivatives from Olives," *Phytochemistry*, Nov. 1998, pp. 1311–1315, vol. 49, No. 5.
Visioli, et al., 1995, "Waste waters' from Olive Oil Production are Rich in Natural Antioxidants," *Experientia*, 1995, pp. 32–34, vol. 51.
Ford, et al., 1972, "Preparation of Calcium Elenolate from Olive Press Juice," *Organic Preparations and Procedures*, 1972, pp. 97–104, vol. 4, No. 2.
N/A English Translation of Abstract to RU 2151137, as listed above under Reference, Jun. 20, 2000.
N/A English Translation of Abstract to JP 8119825, as listed above under Reference, May 14, 1996.

* cited by examiner

*Primary Examiner*—Raymond J. Henley, III
(74) *Attorney, Agent, or Firm*—Bromberg & Sunstein LLP

(57) ABSTRACT

The preparation of extracts from olive fruits, olive tree leaves, olive oil as well as olive-press waste. The isolation of natural products from these extracts and the evaluation of the DNA protective antioxidant activity of the extracts and the purified compounds on intact cells.

19 Claims, 4 Drawing Sheets

Compound 1

Compound 2

Compound 3

Compound 4

Compound 5

Compound 6

Compound 7

Compound 8

Compound 9

US 6,906,100 B2

COMPOUNDS AND COMPOSITIONS DERIVED FROM OLIVES AND METHODS OF THE USE THEREOF

CROSS REFERENCE TO RELATED APPLICATIONS

This application claims the priority of Greek patent applications 20020100071 and 20020100072, filed Feb. 8, 2002 in accordance with the provisions of 35 U.S.C. §119. The full disclosure of each of these applications is hereby incorporated by reference herein.

TECHNICAL FIELD AND BACKGROUND ART

The present invention relates to the preparation of extracts from olive fruits, olive tree leaves, olive oil as well as olive-press waste, the isolation of natural products from these extracts and the evaluation of the DNA protection ability versus the antioxidant activity of these extracts and the purified compounds on intact mammalian cells.

Olive oil production, which also uses fresh olives, produces as by-products a solid olive mass, often called "pulp", and wastewater from a water-olive slurry conventionally used in olive oil manufacturing. These olive oil production by-products, are potentially rich in bioactive compounds, but until recently had not been effectively exploited, due to the impracticality of extracting usable amounts of antioxidant compounds using conventional technology. Indeed, although it had been reported that olive oil production wastewater is rich in phenolic antioxidant compounds (Visioli, F., Vinceri, F. F., Galli, C., "Waste waters from olive oil production are rich in natural antioxidants", Experientia, 1995; 51: 32–34), development of a simple and practical method of extracting such compounds from the wastewater lagged.

European Patent Application No. EP 0 811 678 A1 discloses a process for extracting antioxidants from olives, in which olives are crushed, vacuum dried, and pressed to form a cake. The cake is then extracted with a hot medium chain triglyceride or a $C_2$ to $C_6$ alkylene glycol at a pressure of at least 40 bar, to obtain an antioxidant-enriched extract.

U.S. Pat. No. 6,361,803 to Cuomo et al. discloses obtaining antioxidant compounds by extraction of olive oil or whole olives which have been mashed. This patent also identifies as a problem that several inferior grades of, olive oil used in industrial (rather than culinary) applications, and therefore relatively inexpensive compared to culinary grade olive oil, offer potentially rich sources of antioxidant compounds. To date, however, these potential sources of beneficial antioxidants have not been effectively exploited.

PCT Publication WO 02/18310 describes methods for obtaining a hydroxytyrosol-rich composition from vegetation water comprising acidifying olive wastewater and incubating it, then fractionating to separate hydroxytyrosol.

PCT Publication WO 02/16628 describes methods for the enzymatic synthesis of hydroxytyrosol using a tyrosol precursor.

While a significant portion of the literature discusses the antioxidant properties of hydroxytyrosol and other olive oil isolates, certain olive oil isolates have been somewhat overlooked. In some cases, this phenomenon may be because the isolates appear to have little or no anti-oxidant properties per se (particularly when compared to hydroxytyrosol). An example of such a compound is described by Ford, J. H., et al., "Preparation of calcium elenolate from olive press juice", Organic Preparations and Procedures International (1972), 4(2), 97–104.

As a result, other, potentially much more valuable, biological properties of certain olive isolates have heretofore gone undetected and unexploited.

SUMMARY OF THE INVENTION

It is therefore an object of the present application to disclose for the first time heretofore unknown biological properties of compounds which can be isolated from various parts of olive tree products.

In a first embodiment of the invention, there is described the use of olive-derived lactones, for example 2-(5-ethylidene-2-oxo-tetrahydropyran-4-yl) acetic acid, as a cytoprotective agent.

In another embodiment of the invention there is described the use of hydroxytyrosol as a cytoprotective compound.

In still another embodiment of the invention, a purified olive isolate is a lactone having the chemical structure:

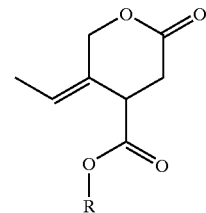

where R=H and lower (i.e. $C_1$–$C_6$) alkyls; the isolate being useful as a cytoprotective agent.

In yet another embodiment of the invention, a purified isolate having the chemical structure:

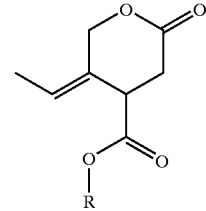

where R=H and is useful as a cytoprotective agent, has the following peaks when it is subjected to NMR: $^1$H(400 MHz; MeOD) δ 2.51 (1H, dd, J=9.5; 16.5 Hz, H-1'a*), 2.64 (1H, dd, J=4.15; 16.45 Hz, H1'b*), 5.64 (1H, q, J=6.5 Hz, H-1"), 1.74 (1H, d, J=7.0 Hz, H-2"), 2.71 (1H, dd, J=6.7; 15.8 Hz, H-3a*), 2.82 (1H, dd, J=6.4; 15.8 Hz, H-3b*), 3.6 (1H, m, H-4), 4.71 (2H, dd, J=12.9; 66.0 Hz, H-6); $^{13}$C (60 MHz; MeOD) δ 35.1 (C-1'a*), 35.1 (C-1'b*), 125.6 (C-1"), 175.8 (C-2), 172.1 (C-2'), 14.2 (C-2"), 38.1 (C-3a*), 38.1 (C-3b*), 30.4 (C-4), 132.1 (C-5), 72.1 (C-6).

In yet another embodiment of the invention there is described a pharmaceutical composition comprising a therapeutically effective amount of 2-(5-ethylidene-2-oxo-tetrahydropyran-4-yl) acetic acid and substituted derivatives thereof for protecting cells.

In still a further embodiment of the invention there is described a pharmaceutical composition comprising a therapeutically effective amount of 2-(5-ethylidene-2-oxo-tetrahydropyran-4-yl) acetic acid, or a substituted derivative thereof, and hydroxytyrosol for use as a cytoprotective.

In a further embodiment of the invention there is described a pharmaceutical composition, wherein said 2-(5- ethylidene-2-oxo-tetrahydropyran-4-yl) acetic acid is extracted from a source selected from the group of olive tree leaves, olive fruit, olive press-waste and olive oil.

In a further embodiment of the invention there is described a use of 2-(5-ethylidene-2-oxo-tetrahydropyran-4-yl) acetic acid to reduce DNA damage suffered by cells exposed to DNA-damaging agents, such as reactive oxidative species and the like.

In still a further embodiment of the invention there is described a use of the compound in pharmaceutical and cosmetic products including the form of tablets, capsules, creams, lotions and ointments.

In still a further embodiment of the invention there is provided use of the compound in pharmaceutical products including solutions, suspensions, foams, shampoos and gels, including hydrogels.

In yet another embodiment of the invention there is provided use of the compounds in pharmaceutical products including epidermal and transdermal delivery systems (patches), buccal delivery systems, transmucosal delivery systems, and more specifically, transmucosal systems for the oral cavity.

And in still another embodiment of the invention there is provided a method of identifying cytoprotective compounds, whether or not anti-oxidative, comprising evaluating a compound isolate by contacting cells with said compound isolate, exposing said cells to a reactive oxidative species, and measuring the extent of DNA damage sustained

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
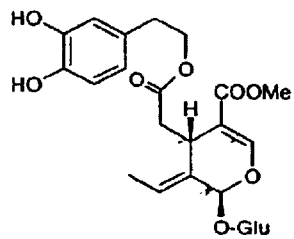
FIG. 1 shows the structural formulas of compounds isolated in the Examples.
Figure 1:
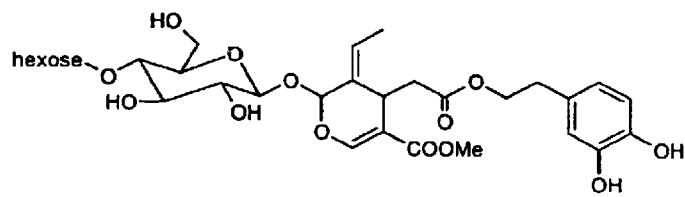
Figure 1:
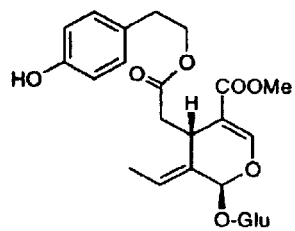
Figure 1:
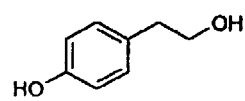
Figure 1:
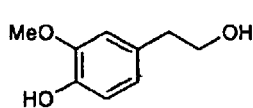
Figure 1:
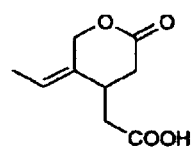
Figure 1:
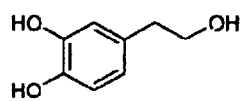
Figure 1:
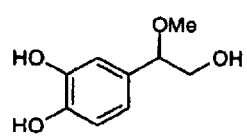
Figure 1:
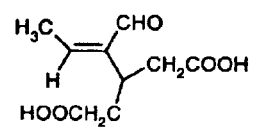

The description below describes exemplary embodiments stemming from the discovery that compounds which can be isolated from various parts of olive trees, fruits thereof, and by-products of various processes, such as olive oil pressing, has DNA-protective, and hence cytoprotective properties. Very surprisingly, one of the compounds which have this property does not apparently operate by scavenging reactive oxidative species.

Throughout the specification and claims, the following terms should be understood as defined here:

Olive isolates are substantially pure samples of a single compound which is derived from an olive tree product, including leaves, bark, olive fruit or drupes, olive oil, and olive oil pressing wastes such as the mashed pulp mass or wastewater.

Cytoprotective isolates are compounds which may be derived from the fruits, leaves, oil or pressings of olive trees and which exhibit an ability to protect cellular DNA from damage, without necessarily having a reducing effect on reactive oxidative species. Without wishing to be bound to any particular theory of mechanism, it is hypothesized that the isolates of the present invention may operate to cause DNA damage to be less than in untreated controls by such mechanisms as preventing free radical production although alternate theories might include somehow reducing membrane permeability to DNA damaging conditions, or by activating or strengthening a cell's natural defenses against DNA damaging conditions.

Anti-oxidant means a compound which reduces reactive oxidative species upon contact with same.

Therapeutic effect and protection should be understood as being any measurable reduction in DNA damage or mortality among cells brought into contact with compounds of the invention and either simultaneously or within a time proximate thereto are exposed to a particular damaging agent, as compared to the DNA damage or mortality experienced by similar cells exposed to the damaging agent without first or simultaneously therewith being contacted with a cytoprotective compound of the invention.

Preparation of Extract From Olive Tree Leaves

A number of varieties were studied (koroneiki, megaritiki, agouromanaki and amfissis). For example, an acetone extraction was carried out on a 6 kg sample of olive tree leaves of the koroneiki variety. The extract underwent solvent removal, under vacuum, to obtain a dry residue termed Extract I. Extract I was then washed with a dichloromethane/methanol solution in a 98/2 vol.:vol.ratio, to give a residue rich in oleuropein (Compound 1 in FIG. 1). The latter was then subjected to liquid chromatography, where a vacuum system was applied to the column and resulted in the isolation of 100 mg of pure oleuropein. In addition, 80 mg of oleuropein diglycoside (Compound 2 in FIG. 1) and 40 mg of 3"-deoxyoleuropein or ligstroside (Compound 3 in FIG. 1) were also obtained in pure form. Similar results were also found for the remaining aforementioned varieties.

Extract from Olive Fruits

A 2 kg sample series of olive fruits (koroneiki, megaritiki, agouromanaki and amfissis varieties) were extracted with methanol and dried under reduced pressure yielding Extract II.

Extract from Olive Oil

A 500 ml sample of olive oil was diluted with 1000 ml of cyclohexane followed by methanol addition. Extraction was then carried out in a methanol/cyclohexane immiscible system and the methanol phase was concentrated to a dry weight of 125 mg and termed Extract III.

Extract from Olive-Press Biomass Residue

The oil-press waste was selected from a "tri-phasic" olive-press system of the largest Greek olive crop variety, the koroneiki. A tri-phasic olive-press system employs water during the kneading phase. A 1 L liquid sample of waste was first filtered so as to remove any solid waste, and then extracted twice with cyclohexane (2×500 ml). The aqueous phase was further extracted with ethyl acetate (EtOAc) three times (3×500 ml). The organic phase was separated and dried under reduced pressure. With reference to the flow chart in FIG. 2, the resulting 2.1 g of solid residue, labeled Extract IV, was subjected to chromatographic separation with the use of medium pressure liquid chromatography (MPLC), incorporating a silica gel 60H stationary phase and, as a liquid phase, a solvent system of increasing gradients of dichloromethane and methanol ($CH_2Cl_2$/MeOH) so as to fractionally increase the polarity thereof. The resulting fractions 1–13 were analyzed by thin layer chromatography (TLC), using aluminum-coated plates as well as, normal and reverse (RP-18) phase glass-coated plates. The TLC plates were then analyzed under a UV lamp and were sprayed with a sulfuric acid—vanillin mixture. Fractions 3, 7, 9 and 11 were then subjected to liquid chromatography (LC) and preparative (PTLC) chromatographic techniques (see FIG. 2) with the use of a $CH_2Cl_2$/MeOH mobile phase of differing polarities so that the following compounds (as labeled and shown in FIG. 1) were obtained in pure form:

Compound 4: Tyrosol (yield=100 mg/L)

Compound 5: 3-methoxytyrosol (yield=70 mg/L)

Compound 6: 2-(5-ethylidene-2-oxo-tetrahydropyran-4-yl) acetic acid (yield=200 mg/L)

Compound 7: hydroxytyrosol (yield=300 mg/L)

Compound 8: 2-methoxy-2-(3,4-dihydroxy-phenyl) ethanol (yield=30 mg/L) and

Compound 9: 3-[1-(formyl)-(E)-1-propenyl]-glutaric acid (yield=300 mg/L).

The structural elucidation of the aforementioned compounds was carried out by UV and NMR (1D and 2D) spectral analysis as well as, by mass spectroscopy.

The chemical data for compounds 1–5 and 7–9 has been published. The NMR data for the only lactone isolated, 2-(5-ethylidene-2-oxo-tetrahydropyran-4-yl) acetic acid or Compound 6 is as follows:

$^1$H(400 MHz; MeOD) δ 2.51 (1H, dd, J=9.5; 16.5 Hz, H-1'a*), 2.64 (1H, dd, J=4.15; 16.45 Hz, H-1'b*), 5.64 (1H, q, J=6.5 Hz, H-1"), 1.74 (1H, d, J=7.0 Hz, H-2"), 2.71 (1H, dd, J=6.7; 15.8 Hz, H-3a*), 2.82 (1H, dd, J=6.4; 15.8 Hz, H-3b*), 3.6 (1H, m, H-4), 4.71 (2H, dd, J=12.9; 66.0 Hz, H-6); $^{13}$C (60 MHz; MeOD) δ 35.1 (C-1'a*), 35.1 (C-1'b*), 125.6 (C-1"), 175.8 (C-2), 172.1 (C-2'), 14.2 (C-2"), 38.1 (C-3a*), 38.1 (C-3b*), 30.4 (C-4), 132.1 (C-5) 72.1 (C-6).

The mass spectrometry results were as follows: m/z (EI) 184. [Found: M+H, 185, $C_9H_{12}O_4$].

Using a similar approach, the same compounds were isolated from a "bi-phasic" olive-press system. A bi-phasic olive-press system uses the olive juice during the kneading process, without the addition of water. It is to be noted that the chemical composition of the waste products has been found to differ significantly, depending on the variety and time of harvest.

Fractionation Method in the Extraction of The Waste Residue from the Koroneiki Variety 1. A 300 ml sample obtained from the lowest layer of waste 2. Extraction with cyclohexane and rejection of the organic layer 3. Multiple extraction of the aqueous layer with ethyl acetate and collection of the organic layers 4. Solvent evaporation and weighing of dry residue 5. Chromatographic separations Study of Antioxidant Activity In the analysis of the antioxidant activity of the extracts I, II, III and IV, as well as, of the pure Compounds 1–9, a method based on measuring the relative protection of DNA of intact cells was performed. This was done with the use of Jurkat cell cultures (a cell line of T-lymph-cells), which were grown in RPMI-1640 enriched with fetal bovine calf serum (10%), penicillin, streptomycin and glutamine. The cells were incubated with the extracts and the purified compounds in the presence of glucose oxidase (60 ng/100 ml) used for the generation of $H_2O_2$. After exposure of the cells to $H_2O_2$ for 10 min, the degree of DNA damage was evaluated using a specialized method, "single cell gel electrophoresis", also known as the "comet assay". The comet assay method is described in the following references: 1. Barbouti A. et al., "DNA Damage And Apoptosis In Hydrogen Peroxide-Exposed Jurkat Cells: Bolus Addition Versus Continuous Generation Of $H_2O_2$," Free Radical Biology and Medicine, 33(5): 691–702, Elsevier Press (2002); as well as Panagiotidis M. et al. (1999) Free Radical Biology and Medicine, 26(5–6): 548–556; Doulias P-T. et al. (2001) Free Radical Biology and Medicine, 30(6): 679–685; Tselepis A. et al. (2001) Free Radical Biology and Medicine, 30(12): 1357–1364; and Barbouti A. et al. (2001) Free Radical Biology and Medicine, 31(4): 490–498 5.

The comet assay reveals the protective effects of pure compounds or mixtures of compounds on the DNA damage induced during exposure of the cells to oxidative stress.

Jurkat cells—a cell line of lymphocytic origin—were exposed to continuously generated hydrogen peroxide, $H_2O_2$ and the effects of this treatment on cellular DNA was evaluated according to the references above. Pretreatment of the same cells with the compound (or mixture of compounds) under evaluation at various concentrations before the addition of $H_2O_2$ leads to decreased DNA damage if the compound has cell protective properties.

The graphic results of the "comet assay" for the waste water extract (IV) and tyrosol (Compound 4), 2-(5-ethylidene-2-oxo-tetrahydropyran-4-yl) acetic acid (from the compound class of lactones or Compound 6) and hydroxytyrosol (Compound 7) are depicted below in FIGS. 3–6, respectively. Open bars denote the absence, while solid bars the presence of the enzyme "glucose oxidase" (GO) which generates $H_2O_2$ at a rate of 10 μM/min. The values are expressed as mean ±SD (n=3).

According to the results, of the pure compounds only 2-(5-ethylidene-2-oxo-tetrahydropyran-4-yl) acetic acid and hydroxytyrosol (but not tyrosol) showed strong protective activity on cells, against oxidative stress, as in their presence, the DNA damage induced is decreased. 2-(5-ethylidene-2-oxo-tetrahydropyran-4-yl) acetic acid (referred to as "lactone" in the figure, above) exerts a dose-dependent protection. It is notable that this compound does not show any antioxidant ability when tested by usual chemical methods (e.g. DPPH). It is thus postulated that 2-(5-ethylidene-2-oxo-tetrahydropyran-4-yl) acetic acid prevents the generation of free radicals rather than scavenging them after their production, though we do not wish to be bound by this theory.

As expected, as it contains both of these substances, protective action was also observed with the extract obtained from the waste material (extract IV), whereas this was not observed with extracts I–III.

Figure 2:
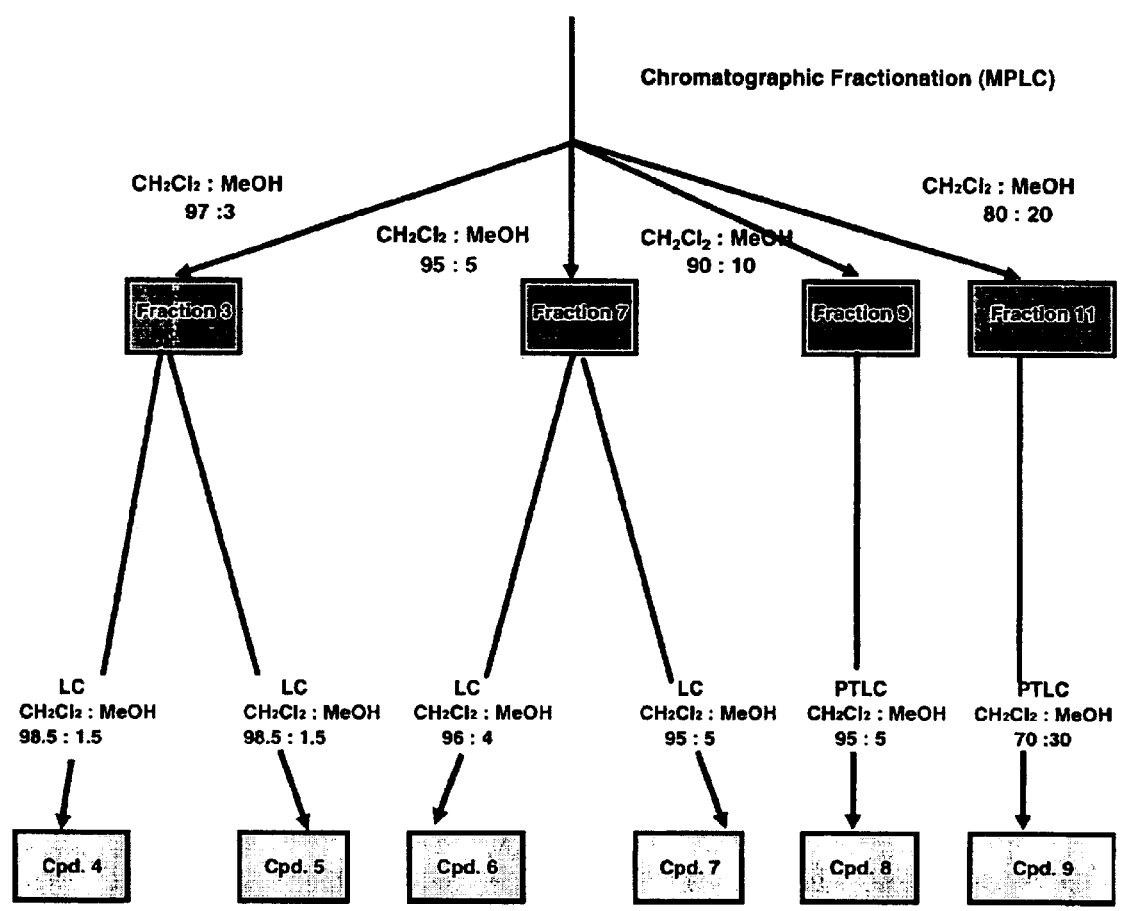
FIG. 2 is a flow chart showing the paths for the chromatographic fractionation of the extracts.
Figure 3:
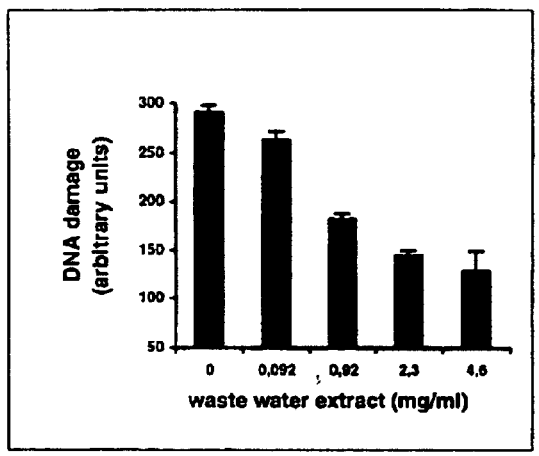
FIG. 3 shows the comet assay results of olive press wastewater extract.
Figure 4:
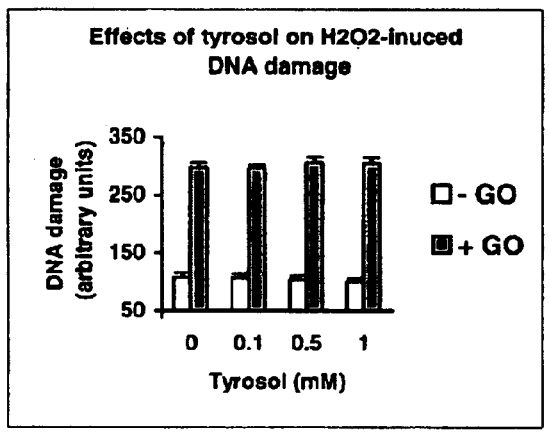
FIG. 4 shows the comet assay results of tyrosol.
Figure 6:
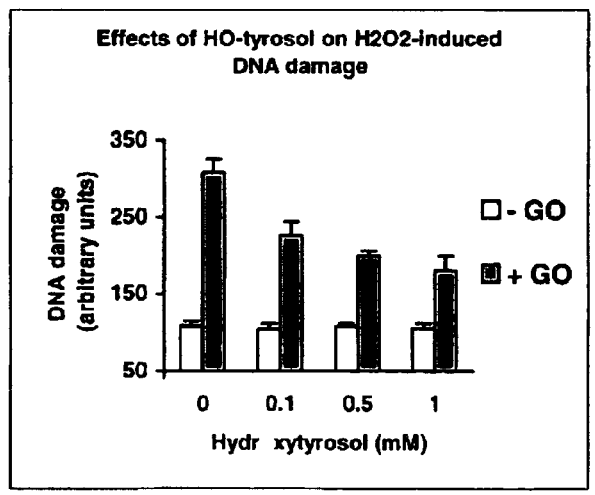
FIG. 6 shows the comet assay results of hydroxytyrosol.
Figure 5:
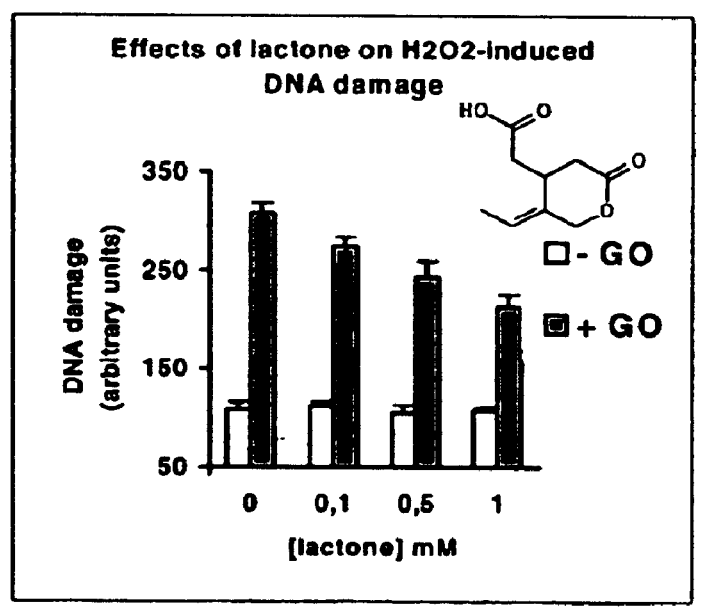
FIG. 5 shows the comet assay results of the lactone, 2-(5-ethylidene-2-oxo-tetrahydropyran-4-yl) acetic acid.

The olive-press waste can be considered as a very important source of 2-(5-ethylidene-2-oxo-tetrahydropyran-4-yl) acetic acid (Compound 6 in FIG. 1), as well as of hydroxytyrosol (Compound 7 in FIG. 1). The antioxidant and cytoprotective properties of these compounds of natural origin, render them as raw materials of great importance to the pharmaceutical, cosmetic and food industry.

Geno-Toxic and Geno-Protective Properties of Olive Oil:

While it appears that unpurified extracts of olive oil also exerts some protective effects, it is apparent from the increased DNA damage observed and induced in the absence of $H_2O_2$, the unpurified olive oil extracts also contain genotoxic compounds.

Figure 7:
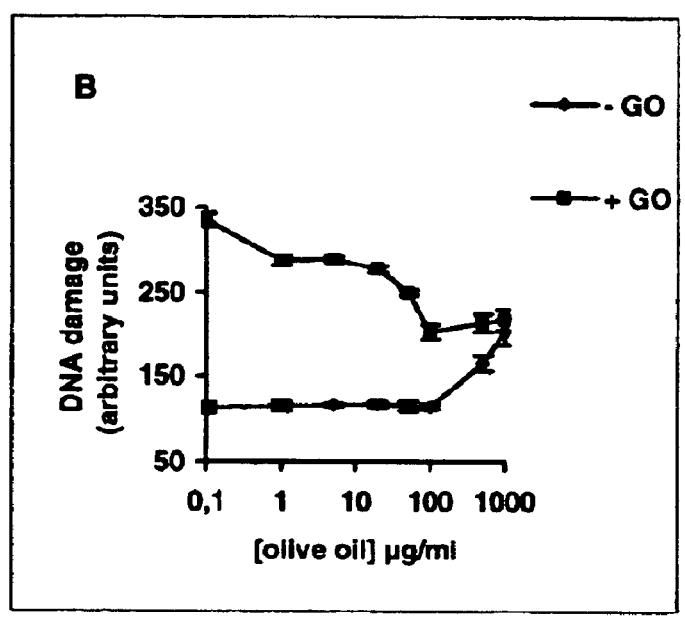
FIG. 7 shows the genotoxicity of unpurified olive oil extracts at concentrations above 100 $\mu$g/ml.

The lower line in FIG. 7 was obtained in the absence of $H_2O_2$ production. As can be seen, there is a certain degree of DNA damage even in the absence of $H_2O_2$. The degree of damage increases significantly at concentrations of the olive oil extract higher than 100 µM/ml.

Thus, it is preferable to isolate those active compounds with little or no genotoxic properties.

Contact between the cytoprotective compounds identified herein and the cells to be protected, whether the cells are part of a culture or in an animal or human subject, may be achieved by formulating the compound, singly or in combination with other cytoprotective or anti-oxidant compounds in various pharmaceutical and cosmetic dosage forms. The group of available dosage forms includes tablets (immediate release, controlled release or extended release), capsules, oils, creams, ointments, solutions, suspensions, shampoos, and gels. Dosage forms may be made for various routes of administration including oral, subcutaneous, intravenous, epidermal and transdermal systems (patches), buccal systems, transmucosal systems, and more specifically, transmucosal systems for the oral cavity.

What is claimed is:

1. A composition for cytoprotection comprising a cytoprotective amount of an isolated, purified compound having the structure:

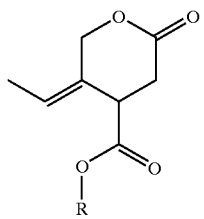

where R may be selected from the group consisting of H and $C_1$–$C_6$ substituted and unsubstituted alkyls.

2. A composition for cytoprotection according to claim 1, wherein R is H.

3. A composition according to claim 1, wherein said compound is extracted from a source selected from the group of olive tree leaves, olive fruit, olive press-waste and olive oil.

4. A composition according to claim 1, wherein said composition is provided in a dosage form selected from the group consisting of tablets, capsules, oils, creams, ointments, solutions, suspensions, shampoos, foams, hydrogels, gels, epidermal systems, transdermal systems, transmucosal systems, and parenteral systems.

5. A composition according to claim 1, further comprising at least one antioxidant.

6. A composition according to claim 5, wherein the antioxidant is hydroxytyrosol or tyrosol.

7. A composition according to claim 4, wherein said composition is provided in a dosage form selected from the group consisting of buccal systems, intravenous systems, intra-muscular systems, and subcutaneous systems.

8. A composition according to claim 1, wherein said composition is provided in a dosage form suitable for administration in a manner selected from the group consisting of oral, intra-oral, epidermal, transdermal, transmucosal, and parenteral.

9. A composition according to claim 8, wherein said composition is provided in a dosage form suitable for administration in a manner selected from the group consisting of intravenous, intra-muscular, and subcutaneous.

10. A composition according to claim 1, wherein said composition is at least one of a pharmaceutical composition and a cosmetic composition.

11. A composition for cytoprotection having a therapeutic amount of an isolated, purified compound having the following peaks when subjected to NMR: $^1H$(400 MHz; MeOD) δ 2.51 (1H, dd, J=9.5; 16.5 Hz, H-1'a*), 2.64 (1H, dd, J=4.15; 16.45 Hz, H-1'b*), 5.64 (1H, q, J=6.5 Hz, H-1"), 1.74 (1H, d, J=7.0 Hz, H-2"), 2.71 (1H, dd, J=6.7; 15.8 Hz, H-3a*), 2.82 (1H, dd, J=6.4; 15.8 Hz, H-3b*), 3.6 (1H, m, H-4), 4.71 (2H, dd, J=12.9; 66.0 Hz, H-6); $^{13}C$ (60 MHz; MeOD) δ 35.1 (C-1'a*), 35.1 (C-1'b*), 125.6 (C-1"), 175.8 (C-2), 172.1 (C-2'), 14.2 (C-2"), 38.1 (C-3a*), 38.1 (C-3b*), 30.4 (C-4), 132.1 (C-5), 72.1 (C-6).

12. A method for protecting the DNA of living cells from damage caused by reactive oxidative species, the method comprising administering the composition according to claim 2.

13. A method for protecting cells from damage due to oxidative stress comprises contacting said cells with a compound having the following structure:

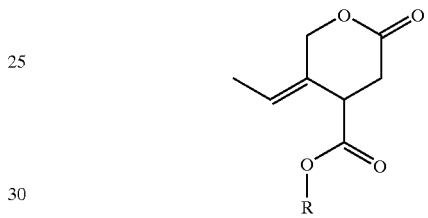

where R may be selected from the group consisting of H and $C_1$–$C_6$ substituted and unsubstituted alkyls.

14. The method for protecting cells according to claim 13, wherein said compound is in a dosage form selected from the group consisting of tablets, capsules, oils, creams, ointments, solutions, suspensions, shampoos, foams, hydrogels, gels, epidermal systems, transdermal systems, transmucosal systems, and parenteral systems.

15. The method for protecting cells according to claim 13, wherein said compound is administered by a route or system selected from the group consisting of oral, intra-oral, epidermal, transdermal, transmucosal, and parenteral.

16. The method according to claim 14, wherein said compound is in a dosage form selected from the group consisting of buccal systems, intravenous systems, intra-muscular systems, and subcutaneous systems.

17. The method according to claim 15, wherein said compound is administered by a route or system selected from the group consisting of intravenous, intra-muscular, and subcutaneous.

18. A method according to claim 13, wherein said compound is in the form of at least one of a pharmaceutical composition and a cosmetic composition.

19. A method of identifying a compound as cytoprotective comprising contacting Jurkat cells with said compound, exposing said cells to a reactive oxidative species for a time period, and measuring the extent of DNA damage sustained using the comet assay.

* * * * *

UNITED STATES PATENT AND TRADEMARK OFFICE
CERTIFICATE OF CORRECTION

PATENT NO.       : 6,906,100 B2
APPLICATION NO.  : 10/364305
DATED            : June 14, 2005
INVENTOR(S)      : Spiros Fotinos et al.

It is certified that error appears in the above-identified patent and that said Letters Patent is hereby corrected as shown below:

Column 2,
Lines 21-30 and 35-44, replace

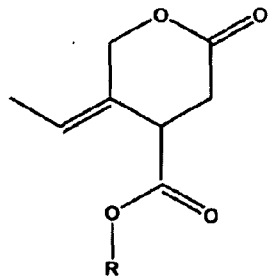   with   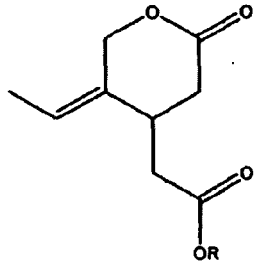

Column 7,
Lines 23-31, replace

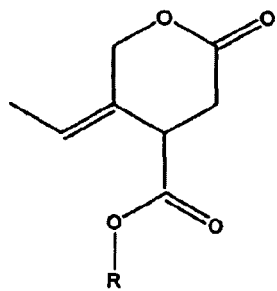   with   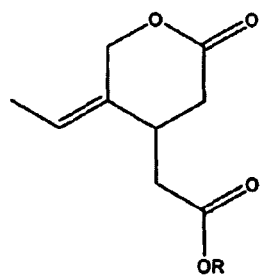

UNITED STATES PATENT AND TRADEMARK OFFICE
CERTIFICATE OF CORRECTION

PATENT NO. : 6,906,100 B2  Page 2 of 2
APPLICATION NO. : 10/364305
DATED : June 14, 2005
INVENTOR(S) : Spiros Fotinos et al.

It is certified that error appears in the above-identified patent and that said Letters Patent is hereby corrected as shown below:

Column 8,
Lines 23-31, replace

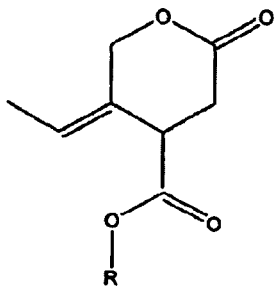   with   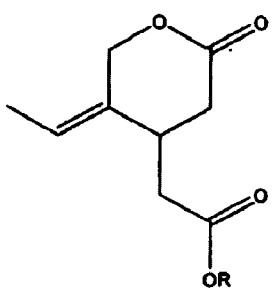

Signed and Sealed this

Eleventh Day of July, 2006

JON W. DUDAS
*Director of the United States Patent and Trademark Office*